(12) United States Patent
Niikura

(10) Patent No.: US 10,315,189 B2
(45) Date of Patent: Jun. 11, 2019

(54) ETHOXYLATION CATALYST AND MANUFACTURING METHOD THEREFOR

(71) Applicant: LION CORPORATION, Tokyo (JP)

(72) Inventor: Fumiya Niikura, Tokyo (JP)

(73) Assignee: Lion Corporation, Tokyo (JP)

( * ) Notice: Subject to any disclaimer, the term of this patent is extended or adjusted under 35 U.S.C. 154(b) by 0 days.

(21) Appl. No.: 15/756,962

(22) PCT Filed: Sep. 5, 2016

(86) PCT No.: PCT/JP2016/075959
§ 371 (c)(1),
(2) Date: Mar. 1, 2018

(87) PCT Pub. No.: WO2017/039011
PCT Pub. Date: Mar. 9, 2017

(65) Prior Publication Data
US 2018/0243730 A1 Aug. 30, 2018

(30) Foreign Application Priority Data

Sep. 4, 2015 (JP) .................................. 2015-174742

(51) Int. Cl.
| | |
|---|---|
| *B01J 23/02* | (2006.01) |
| *B01J 27/053* | (2006.01) |
| *B01J 37/08* | (2006.01) |
| *B01J 35/10* | (2006.01) |
| *C07C 67/03* | (2006.01) |
| *C07C 69/24* | (2006.01) |
| *C07B 61/00* | (2006.01) |

(52) U.S. Cl.
CPC ............. *B01J 27/053* (2013.01); *B01J 35/10* (2013.01); *B01J 35/1014* (2013.01); *B01J 35/1019* (2013.01); *B01J 37/08* (2013.01); *C07C 67/03* (2013.01); *C07B 61/00* (2013.01); *C07C 69/24* (2013.01)

(58) Field of Classification Search
CPC ...... B01J 27/053; B01J 35/10; B01J 35/1014; B01J 35/1019; B01J 37/08; C07C 67/03; C07C 69/24; C07B 61/00
USPC ........................... 502/217; 423/544, 549, 555
See application file for complete search history.

(56) References Cited

U.S. PATENT DOCUMENTS

| | | | | |
|---|---|---|---|---|
| 2,595,943 A | * | 5/1952 | Heinz ...................... | B01J 20/12 127/46.1 |
| 3,822,340 A | * | 7/1974 | Eberl et al. ............. | B29C 70/10 423/555 |
| 4,101,638 A | * | 7/1978 | Inoue ...................... | C01B 25/22 423/320 |
| 4,362,651 A | | 12/1982 | Schwarzenbek | |
| 4,754,075 A | * | 6/1988 | Knopf .................. | B01J 31/1805 568/606 |
| 4,946,984 A | | 8/1990 | Hauser | |
| 5,093,093 A | * | 3/1992 | Koslowski ........... | A01K 1/0154 106/778 |
| 5,840,995 A | | 11/1998 | Mayer et al. | |
| 6,689,375 B1 | * | 2/2004 | Wahlig ................ | A61L 24/0042 424/423 |
| 7,824,490 B2 | * | 11/2010 | Bruce ................... | C04B 11/007 106/772 |
| 2015/0158735 A1 | * | 6/2015 | Wu .......................... | C08K 7/08 428/401 |

FOREIGN PATENT DOCUMENTS

| | | | | | |
|---|---|---|---|---|---|
| JP | 02-134336 | | * | 5/1990 | ............. C07C 43/10 |
| JP | 03-215446 | | * | 9/1991 | ............. C07C 43/13 |
| JP | 09-201534 | | * | 8/1997 | ............. B01J 31/02 |
| JP | 2008-510614 | | * | 4/2008 | ............. B01J 31/26 |
| WO | 85/00365 | | | 1/1985 | |
| WO | 2006/025898 A1 | | | 3/2006 | |
| WO | 2013/154189 A1 | | | 10/2013 | |

OTHER PUBLICATIONS

Japanese Patent Office, "International Search Report" in connection with related International Application No. PCT/JP2016/075959, dated Nov. 29, 2016, 4 pages.
Fischbach, Malaika, Examiner, European Patent Office, "Extended European Search Report" in connection with related European Patent App. No. 16842040.4, dated Mar. 15, 2019, 7 pgs.
Ling, Yuanbing et al., "Preparation of α-Calcium Sulfate Hemihydrate by Reaction of Sulfuric Acid with Lime", Industrial & Engineering Chemistry Research, vol. 44, No. 4, Feb. 1, 2005, pp. 715-724.

* cited by examiner

*Primary Examiner* — Patricia L. Hailey
(74) *Attorney, Agent, or Firm* — Kolisch Hartwell, P.C.

(57) ABSTRACT

Disclosed is an ethoxylation catalyst having a BET specific surface area of 40 to 150 m²/g and including calcium sulfate particles including at least one kind of compound selected from the group consisting of calcium sulfate 0.5 hydrate and type III anhydrous calcium sulfate.

3 Claims, 3 Drawing Sheets

ETHOXYLATION CATALYST AND MANUFACTURING METHOD THEREFOR

TECHNICAL FIELD

The present invention relates to an ethoxylation catalyst and a manufacturing method therefor.

Priority is claimed on Japanese Patent Application No. 2015-174742 filed in Japan on Sep. 4, 2015, the content of which is incorporated herein by reference.

BACKGROUND

Alkylene oxide adducts of an organic compound having active hydrogen or derivatives thereof are widely used as solvents, surfactants, or various chemical intermediates. In particular, alkylene oxide adducts obtained by adding an alkylene oxide such as ethylene oxide or propylene oxide to alcohols, fatty acids, fatty acid alkyl esters, amines, alkylphenols, or the like are widely used as nonionic surfactants.

For example, a fatty acid alkyl ester alkoxylate obtained by adding an alkylene oxide to a fatty acid alkyl ester and an alcohol alkoxylate obtained by adding an alkylene oxide to an alcohol are frequently used as a washing component of a detergent.

Examples of a method for manufacturing the alkylene oxide adduct include a method in which an alkylene oxide is added to a fatty acid alkyl ester or an alcohol in the presence of an alkoxylation catalyst.

In the above manufacturing method, it is known that the properties of the alkylene oxide adduct to be obtained and the amount of by-products produced vary depending on the alkoxylation catalyst. For example, in a case where an alkaline catalyst is used as the alkoxylation catalyst described above, it is possible to obtain an alkylene oxide adduct having a wide adduct distribution of alkylene oxide. In a case where a solid metal catalyst is used as the alkoxylation catalyst described above, it is possible to obtain an alkylene oxide adduct having a narrow adduct distribution of alkylene oxide. Therefore, studies on alkoxylation catalysts are being actively conducted in order to obtain a desired alkylene oxide adduct.

PTL 1 discloses an alkoxylation catalyst obtained by reacting at least one compound selected from the group consisting of an alkaline earth metal salt of a carboxylic acid, an alkaline earth metal salt of a hydroxycarboxylic acid, an oxide of an alkaline earth metal, and a hydroxide of an alkaline earth metal with sulfuric acid in a liquid dispersion medium. It is described that the amount of by-products produced is reduced in a case where the alkylene oxide adduct is manufactured using the alkoxylation catalyst.

CITATION LIST

Patent Literature

[PTL 1] PCT International Publication No. WO2013/154189

SUMMARY

Technical Problem

However, in a case where an alkylene oxide adduct is manufactured using the catalyst disclosed in PTL 1, there is a period (induction period) in which the alkoxylation reaction hardly proceeds even when a reaction raw material and a catalyst are added to a reactor and alkylene oxide is introduced into the reactor to bring the reaction raw material and alkylene oxide into contact with each other. Therefore, there is a problem in that the time required for the alkoxylation reaction becomes long. Furthermore, the catalyst disclosed in PTL 1 is a dispersion liquid and the handling property during transporting and storing is not good.

The present invention has been made in view of the above circumstances and an object of the present invention is to provide an ethoxylation catalyst which has a shorter induction period and which has an excellent handling property.

Solution to Problem

As a result of intensive studies, the present inventors found that the following ethoxylation catalyst is able to solve the problems described above.

That is, the present invention has the following configuration.

[1] An ethoxylation catalyst having a BET specific surface area of 40 to 150 m2/g, the catalyst including calcium sulfate particles including at least one kind of compound selected from the group consisting of calcium sulfate 0.5 hydrate and type III anhydrous calcium sulfate.

[2] A method for manufacturing an ethoxylation catalyst, the method including a reacting step of mixing at least one compound (A) selected from the group consisting of calcium salt of carboxylic acid, calcium oxide, and calcium hydroxide with sulfuric acid (B) in a solvent (C) to produce a reaction product of (A) and (B), then a separating step of separating the reaction product from the solvent (C), and a drying step of drying the reaction product separated in the separating step, in which the solvent (C) is an alcohol having 1 to 6 carbon atoms, a molar ratio of (B) to (A) added to the solvent (C) is from 0.5 to 0.99, and a drying temperature in the drying step is less than 400° C.

[3] The method for manufacturing an ethoxylation catalyst according to [2], in which the drying temperature in the drying step is 50° C. to 350° C.

[4] A method for manufacturing an ethoxylated reaction product, in which an ethoxylated reaction product is obtained by bringing the ethoxylation catalyst of [1] and ethylene oxide into contact with a fatty acid alkyl ester or alcohol.

Advantageous Effects of Invention

According to the ethoxylation catalyst of the present invention, the induction period is further shortened and the handling property is excellent.

DESCRIPTION OF EMBODIMENTS

Ethoxylation Catalyst

The ethoxylation catalyst of the present invention (also referred to below simply as "catalyst") is calcium sulfate particles including at least one compound selected from the group consisting of calcium sulfate 0.5 hydrate (also referred to below simply as "0.5 hydrate") and a type III anhydrous calcium sulfate (also referred to below as "type III anhydrate").

The BET specific surface area of the catalyst of the present invention is 40 to 150 $m^2/g$.

Calcium Sulfate Particles

The calcium sulfate particles include at least one kind of compound selected from the group consisting of a 0.5 hydrate ($CaSO_4 \cdot 0.5 H_2O$) and a type III anhydrate ($CaSO_4$). Below, the at least one kind of compound selected from the group consisting of a 0.5 hydrate and a type III anhydrate is referred to as a "0.5 hydrate or the like".

Since the catalyst of the present invention is calcium particles including a 0.5 hydrate or the like, it is possible to shorten the induction period in the ethoxylation reaction.

In addition to the 0.5 hydrate and type III anhydrate described above, calcium sulfates are known to include calcium sulfate dihydrate ($CaSO_4 \cdot 2H_2O$, simply referred to below as "dihydrate") and type II anhydrous calcium sulfate ($CaSO_4$, also referred to below as "type II anhydrate").

These change as the calcium sulfate is heated, absorbs moisture, or the like. For example, according to the following reference literature, when dihydrate is dry heated at 130° C., the dihydrate becomes a 0.5 hydrate and when further dry heated at 190° C., becomes a type III anhydrate. When the type III anhydrate is further heated, the type III anhydrate becomes a type I anhydrate. The type III anhydrate easily absorbs water vapor in the air and returns to being a 0.5 hydrate, while the type II anhydrate does not easily return to being a 0.5 hydrate.

Toshio Takahashi and two others, "Manufacturing Test of Wood Gypsum Board (6)", Forestry and Forest Products Research Institute monthly report, December 1979.

It is possible to determine whether the calcium sulfate particles include any kind of the calcium sulfate, for example, by performing X-ray diffraction (XRD) measurement.

Figure 1A:
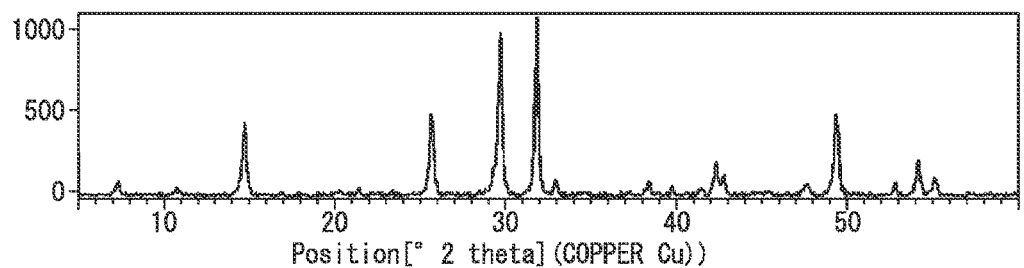
FIG. 1A is a diffraction pattern obtained when carrying out X-ray diffraction measurement on calcium sulfate which is a 0.5 hydrate.
Figure 1B:
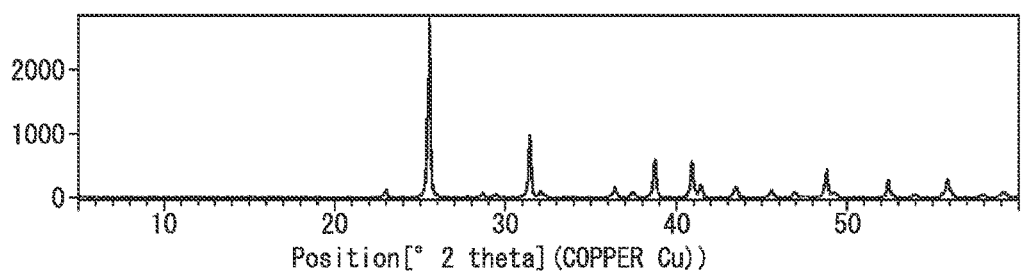
FIG. 1B is a diffraction pattern obtained when carrying out X-ray diffraction measurement on calcium sulfate which is a type II anhydrate.
Figure 1C:
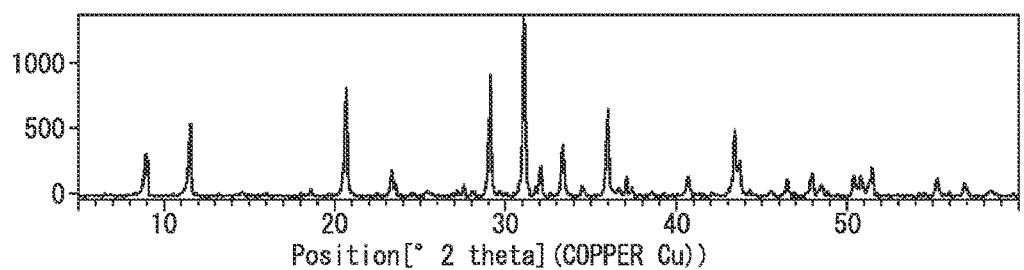
FIG. 1C is a diffraction pattern obtained when carrying out X-ray diffraction measurement on calcium sulfate which is a dihydrate.

FIG. 1A is an example of an XRD pattern of a 0.5 hydrate. FIG. 1B is an example of an XRD pattern of a type II anhydrate. FIG. 1C is an example of an XRD pattern of a dihydrate. As described above, since the type III anhydrate easily absorbs water vapor in the air and returns to being a 0.5 hydrate, the XRD pattern of the type III anhydrate is considered to be the same as in FIG. 1A.

It is possible to determine which kind of the calcium sulfates described above are included in the calcium sulfate particles by performing XRD measurement of the calcium sulfate particles to be determined and determining which of FIG. 1A, FIG. 1B, and FIG. 1C the obtained XRD pattern is similar to.

For example, if an XRD pattern similar to that in FIG. 1A is obtained, it is possible to determine that the calcium sulfate particles include a 0.5 hydrate or the like. Similarly, if an XRD pattern similar to that of FIG. 1B is obtained, it is possible to determine that the calcium sulfate particles include a type II anhydrate, and, if an XRD pattern similar to that of FIG. 1C is obtained, it is possible to determine that the calcium sulfate particles include a dihydrate.

It is possible to adjust the content of the 0.5 hydrate or the like in the calcium sulfate particles by adjusting the molar ratio of (A) and (B) to be added to the specific solvent (C), by adjusting the drying temperature in the drying step, or the like, in the method for manufacturing the catalyst described below.

It is possible to measure the content of the 0.5 hydrate or the like in the calcium sulfate particles in the present invention, for example, by an apparatus using the XRD measurement method (for example, "X'Pert PRO MRD apparatus" manufactured by PANalytical).

In addition, the conditions of the XRD measurement in the present invention are as described in the Examples.

Here, if the 0.5 hydrate or the like is included in the calcium sulfate particles, when XRD measurement is carried out, peaks specific to a 0.5 hydrate or the like are observed at 2θ=25 to 26°, 29 to 30°, and 32°. The peak intensity of the peaks varies depending on the content of 0.5 hydrate or the like in the calcium sulfate particles.

In the calcium sulfate particles of the present invention, the peak intensity of a peak observed at 25° to 26° is preferably smaller than the peak intensity of a peak observed at 29° to 30°. Using such calcium sulfate particles further shortens the induction period.

BET Specific Surface Area

The BET specific surface area of the catalyst of the present invention is 40 to 150 $m^2/g$. When the BET specific surface area is within the above range, the induction period is shortened.

The BET specific surface area of the catalyst of the present invention is preferably 50 to 150 $m^2/g$, and more preferably 60 to 150 $m^2/g$.

The BET specific surface area of the catalyst is adjusted by changing the kind of the solvent (C), adjusting the drying temperature, or the like, in the method for manufacturing a catalyst described below.

In addition, the BET specific surface area in the present invention is measured by the method described in the Examples.

The average particle size of the catalyst of the present invention is not particularly limited, but, for example, is preferably 1 μm to 100 μm, and more preferably 1 μm to 50 μm.

The catalyst of the present invention is suitable as a catalyst for an ethoxylation reaction from the viewpoint that the induction period is further shortened and it is easy to obtain the effect of the present invention more remarkably.

It is possible to measure the average particle size by a method such as a laser diffraction type particle size distribution measuring apparatus (SALD-3100, manufactured by Shimadzu Corporation).

Method for Manufacturing Catalyst

In the method for manufacturing a catalyst of the present invention, at least one compound (A) selected from the group consisting of calcium salt of carboxylic acid, calcium oxide, and calcium hydroxide is mixed with the sulfuric acid (B) in the solvent (C) to produce the reaction product of (A) and (B), and thereafter the reaction product is separated from the solvent (C).

Component (A)

Component (A) is at least one kind of compound selected from the group consisting of calcium salt of carboxylic acid, calcium oxide, and calcium hydroxide.

Examples of calcium salts of a carboxylic acid include calcium acetates such as calcium acetate anhydrate and calcium acetate monohydrate, calcium salts of carboxylic acids having no hydroxy group such as calcium formate, and calcium salts of hydroxycarboxylic acids such as calcium lactate, calcium tartrate, calcium citrate, and calcium malate.

As the component (A), a calcium salt of a carboxylic acid is preferable from the viewpoint of further improving the catalytic activity and the like. As the calcium salt of a carboxylic acid, calcium salts of a carboxylic acid having no hydroxy group are preferable, and among these, calcium acetate is more preferable.

Any one kind of the component (A) may be used alone, or two or more kinds may be used in combination.

Component (B)

Component (B) is sulfuric acid. concentrated sulfuric acid or diluted sulfuric acid may be used as the component (B). Concentrated sulfuric acid (96% by mass or more) is preferable as the component (B) from the viewpoint of stably exhibiting the catalytic activity, and the like.

Component (C)

Component (C) is an alcohol having 1 to 6 carbon atoms. The component (C) is used as a dispersion medium when manufacturing the catalyst of the present invention.

In the present invention, the component (A) and the component (B) are reacted at a specific molar ratio in the component (C) to produce a reaction product, and the reaction product is separated from the component (C) and then dried to obtain a catalyst including calcium sulfate particles containing a 0.5 hydrate and the like and having a specific BET specific surface area.

Examples of the component (C) include alcohols such as methanol, ethanol, 2-propanol (IPA), 1-propanol, 1-butanol, tert-butanol, 1-pentanol, and 1-hexanol. Among these, methanol, ethanol, and IPA are preferable.

Any one kind of the component (C) may be used alone, or two or more kinds may be used in combination.

It is possible to appropriately set the use amount of the component (C) to such a degree that it is possible to disperse the reaction product of the component (A) and the component (B), and it is possible to use 150 to 500 parts by mass with respect to 100 parts by mass of the component (A).

Examples of the method for manufacturing a catalyst of the present invention include a method provided with a dispersing step of dispersing the component (A) in the component (C) to obtain a dispersion, a reacting step of adding the component (B) to the dispersion and mixing the component (A) therein to produce a reaction product of the component (A) and the component (B), then a separating step of separating the reaction product from the component (C), and a drying step of drying the reaction product separated in the separating step.

In the dispersing step, for example, using a reactor provided with a mixing tank provided with a jacket and a paddle stirring blade provided in a stirring tank, the component (C) and the component (A) are added to the stirring tank and stirred to obtain a dispersion in which the component (A) is dispersed in the component (C).

The temperature condition in the dispersing step is not particularly limited, but the temperature is, for example, a normal temperature (5° C. to 35° C.). The temperature inside the stirring tank is adjusted, for example, by passing a heating medium (for example, water) at an arbitrary temperature through the jacket.

The stirring time in the dispersing step is not particularly limited, and is the period of time for the component (A) to be substantially uniformly dispersed in the component (C). Substantially uniform means a state in which it is possible to visually judge that there are no lumps or the like of the component (A) and that the component (A) is uniformly dispersed.

In the reacting step described above, the component (B) is added to the dispersion obtained in the dispersing step, and the component (A) and the component (B) are mixed to produce the reaction product of the component (A) and the component (B) (that is, calcium sulfate particles which are the main catalytically active components).

The method for adding the component (B) in the reacting step is not particularly limited, but, for example, it is preferable to drop the component (B) into the dispersion while stirring the dispersion in the stirring tank.

In the reacting step, the addition amount of the component (B) added to the dispersion is 0.5 to 0.99 as the molar ratio of the component (B) to the component (A) [molar ratio represented by component (B)/component (A), may be referred to below as "B/A ratio"].

When the B/A ratio is within the above range, the induction period is shortened when the catalyst manufactured through the above reacting step is used for the ethoxylation reaction. In addition, calcium sulfate particles including a 0.5 hydrate or the like are easily obtained as a reaction product of the component (A) and the component (B).

Furthermore, in a case where the catalyst manufactured through the reacting step described above is used in the ethoxylation reaction, an alkylene oxide adduct having a narrow adduct distribution of alkylene oxide is easily obtained, and the production of by-products such as high molecular weight PEG is easily suppressed.

The B/A ratio is preferably 0.7 to 0.98, and more preferably 0.8 to 0.98.

In addition, in the reacting step, the mass ratio represented by [component (A)+component (B)]/component (C) [may be referred to below as (A+B)/C ratio] is not particularly limited, but is preferably 1 to 1/3, and more preferably 1 to 1/2.5. When the (A+B)/C ratio is the above lower limit value or more, the content of the components (A) and (B) is not excessively small, and the reaction product of the component (A) and the component (B) is easily obtained. When the (A+B)/C ratio is the above upper limit value or less, it is possible to easily carry out stirring and it is easy to efficiently mix the component (A) and the component (B).

The temperature condition (that is, reaction temperature) in the reacting step is preferably 10 to 70° C., and more preferably 10 to 60° C. If the temperature condition is less than the above lower limit value, there is a concern that the reaction between the component (A) and the component (B) may be delayed and the production efficiency of the catalyst may be lowered. If the temperature condition exceeds the upper limit value above, there is a concern that the catalyst activity of the obtained catalyst may be lowered.

Adjustment of the reaction temperature is carried out, for example, by passing a heating medium (for example, water) at an arbitrary temperature through the jacket.

The stirring time (that is, the reaction time) in the reacting step is the period of time during which the component (A) and the component (B) are able sufficiently react and the time during which it is possible to control heat generation accompanying the addition of the component (B), for example, 1 to 2 hours.

After the reacting step, an aging step may be provided in which the reaction product is stirred at an arbitrary temperature. The temperature condition of the aging step is preferably, for example, 10° C. to 70° C., and more preferably 10° C. to 60° C. Providing the aging step makes it possible to reduce the amount of the unreacted component (A). In addition, the reaction product (calcium sulfate particles) is easily to be obtained in the form of a 0.5 hydrate or a type III anhydrate. Furthermore, it is possible to easily adjust the BET specific surface area of the catalyst within the range of the present invention.

The stirring time (that is, aging time) in the aging step is, for example, 0.5 to 4 hours.

In the separating step, a separating operation for separating the reaction product obtained in the reacting step from the solvent (C) is performed. The separation operation is not particularly limited, and examples thereof include known solid-liquid separation methods. Examples of solid-liquid separation methods include methods using a filter, a filter press, a centrifugal separator, or the like. As the filter, a suction filter or a pressure filter may be used.

The temperature condition of the separating step is not particularly limited and, for example, the liquid temperature of the separation target (separation target) is preferably 10° C. to 70° C., and more preferably 10° C. to 60° C.

The separating step may have a washing operation of washing the reaction product separated by the separating operation with a washing solvent. Examples of washing operations include a method for stirring the reaction product in a washing solvent, and the like. Examples of the washing solvent include alcohols and the like similar to the solvent (C). As the washing solvent, methanol, ethanol, and IPA are preferable.

The separating step may have only a separation operation, or may have a separation operation and a washing operation. In addition, in the separating step, a separation operation and/or a washing operation may be performed twice or more.

The method for manufacturing a catalyst of the present invention is further provided with a drying step.

The drying step is a step of drying the reaction product separated in the separating step. In the drying step, the liquid component is evaporated from the reaction product separated in the separating step.

The drying method is not particularly limited, and, for example, the drying may be carried out by heating and/or reduced pressure, or the drying may be carried out in an environment of normal temperature and normal pressure (natural drying). It is possible to carry out the drying using, for example, a known drying apparatus. Examples of the drying apparatus include a drying apparatus provided with a heating and/or pressure reducing mechanism.

The temperature of the drying step (that is, the drying temperature) is less than 400° C. When the drying temperature is 400° C. or higher, this tends to produce the form of a type II anhydrate. The drying temperature is preferably 390° C. or lower, more preferably 380° C. or lower, even more preferably 350° C. or lower, particularly preferably 330° C. or lower, and most preferably 300° C. or lower. When the drying temperature is the upper limit value or less, a catalyst including a 0.5 hydrate or the like is easily obtained. In addition, the BET specific surface area of the catalyst is easily adjusted within the range of the present invention. On the other hand, the lower limit value of the drying temperature is not particularly limited as long as it is possible to remove the liquid component from the reaction product, but the lower limit value is preferably 0° C. or higher, more preferably 10° C. or higher, even more preferably 20° C. or higher, and particularly preferably 50° C. or higher. When the drying temperature is the lower limit value or more, the time (drying time) required for the drying step is shortened.

The drying temperature is preferably 50° C. to 350° C., more preferably 50° C. to 330° C., and even more preferably 50° C. to 300° C.

The drying time is not particularly limited, but is preferably 0.5 to 24 hours, and more preferably 1 to 12 hours.

Method for Using Catalyst

The catalyst of the present invention is used in an ethoxylation reaction in which ethylene oxide is added to an organic compound to obtain an ethoxylated reaction product. Examples of ethoxylated reaction products include fatty acid alkyl ester ethoxylates and alcohol ethoxylates.

Methods of using the catalyst include a method in which an organic compound as a starting material and a catalyst are added to a reactor provided with stirring blades and stirred to disperse the catalyst in the organic compound, and then ethylene oxide is introduced into the reactor and the organic compound and ethylene oxide are mixed.

The organic compound as a starting material is not particularly limited as long as it is possible to ethoxylate the organic compound and examples thereof include fatty acid alkyl esters (may be referred to below as ($\alpha$) component) or alcohols (may be referred to below as ($\beta$) component).

As the component ($\alpha$), a compound represented by General Formula (I) below is preferable:

$$R^{11}COOR^{12} \quad \quad (I)$$

Where in formula (I), $R^{11}$ is a hydrocarbon group having 1 to 40 carbon atoms, and $R^{12}$ is a linear alkyl group having 1 to 3 carbon atoms.

In formula (I), $R^{11}$ has 1 to 40 carbon atoms, preferably 3 to 30, and more preferably 5 to 21.

$R^{11}$ may be linear or branched.

$R^{11}$ may be a saturated hydrocarbon group (alkyl group) or an unsaturated hydrocarbon group such as an alkenyl group.

In formula (I), $R^{12}$ is a linear alkyl group having 1 to 3 carbon atoms, and more preferably a methyl group having 1 carbon atom.

Examples of the component ($\alpha$) include fatty acid methyl esters such as methyl decanoate, methyl laurate, methyl myristate, and methyl oleate, mixtures thereof, and the like.

As the component ($\beta$), a compound represented by General Formula (II) below is preferable:

$$R^{20}OH \quad \quad (II)$$

Where in the formula (II), $R^{20}$ is a hydrocarbon group having 1 to 40 carbon atoms.

In formula (II), $R^{20}$ has 1 to 40 carbon atoms, preferably 3 to 30, more preferably 6 to 22, and even more preferably 8 to 22.

$R^{20}$ may be linear or branched.

$R^{20}$ may be a saturated hydrocarbon group (alkyl group) or an unsaturated hydrocarbon group such as alkenyl group.

Examples of the component ($\beta$) include higher aliphatic primary alcohols having a saturated or unsaturated linear hydrocarbon group having 8 to 22 carbon atoms such as n-octanol, n-decanol, n-dodecanol, n-tetradecanol, n-hexadecanol, n-octadecanol, oleyl alcohol, eicosanol, behenyl alcohol, nonanol, undecanol, tridecanol and the like;

branched alkyl primary alcohols such as 2-ethylhexanol and Guerbet type alcohols having 16 to 36 carbon atoms; secondary alcohols such as 2-octanol, 2-decanol, and 2-dodecanol: benzyl alcohol, and the like. Among these, higher aliphatic primary alcohols are preferable.

A description will be given below of an example of the method for using the catalyst of the present invention in a case of manufacturing a fatty acid alkyl ester ethoxylate using the catalyst of the present invention.

In the method for manufacturing a fatty acid alkyl ester ethoxylate using the catalyst of the present invention, ethylene oxide is added to the component (a) in the presence of the ethoxylation catalyst of the present invention. Examples of the manufacturing method include a method provided with a catalyst dispersing step, an EO addition reacting step, and an aging step.

The catalyst dispersing step described above is a step of dispersing the ethoxylation catalyst in the component ($\alpha$) which is the starting material. In this step, for example, using a reactor provided with a mixing tank provided with a jacket and a paddle stirring blade provided in a stirring tank, the component ($\alpha$) and the ethoxylation catalyst are stirred in the stirring tank.

The mass ratio represented by ($\alpha$) component/ethoxylation catalyst (may be referred to below as "raw material/catalyst ratio") is, for example, preferably 5 to 10,000, more preferably 10 to 2,000, and even more preferably 20 to 1,000. It is possible to arbitrarily set the raw material/catalyst ratio according to the intended reaction time, but if the raw material/catalyst ratio is small, it may be complicated to separate the catalyst after the reaction.

The temperature condition in this step is not particularly limited, but is, for example, normal temperatures (5° C. to 35° C.). The temperature inside the stirring tank is adjusted, for example, by passing a heating medium (for example, water) of an arbitrary temperature through the jacket.

The stirring time in this step is not particularly limited and is the time for the component ($\alpha$) and the ethoxylation catalyst to become substantially uniform.

The EO addition reacting step is a step of obtaining a fatty acid alkyl ester ethoxylate by adding ethylene oxide to the component ($\alpha$). This step is performed by bringing ethylene oxide into contact with a mixture of the component ($\alpha$) and the ethoxylation catalyst under an arbitrary temperature condition.

In this step, the introduction amount of ethylene oxide with respect to the compound to be ethoxylated (that is, the component ($\alpha$)) is appropriately determined in consideration of the molar number of the ethylene oxide added to the target product and, for example, is preferably 1 to 100 times by mole, more preferably 1 to 80 times by mole, and even more preferably 1 to 50 times by mole.

The temperature condition (addition reaction temperature) of this step is preferably, for example, 160° C. to 180° C.

The pressure condition in this step is appropriately determined taking into consideration the addition reaction temperature and is, for example, preferably 0.1 to 1 MPa, and more preferably 0.1 to 0.6 MPa.

The aging step described above is a step of stirring the inside of the stirring tank at an arbitrary temperature after the addition reacting step. Providing this step make it possible to reduce the amount of unreacted component ($\alpha$).

The temperature condition of this step is, for example, the same as the addition reaction temperature.

Furthermore, as necessary, the catalyst or the like remaining in the fatty acid alkyl ester ethoxylate may be removed.

Examples of methods for removing the catalyst and the like include filtration and the like. Alternatively, it is not necessary to remove the catalyst or the like from the fatty acid alkyl ester ethoxylate.

In the method for using the catalyst described above, a description was given of a case where the fatty acid alkyl ester ethoxylate is manufactured using the catalyst of the present invention, but the present invention is not limited thereto, and alcohol ethoxylates may be manufactured using the catalyst of the present invention and using the component ($\beta$) instead of the component ($\alpha$).

As described above, since the catalyst of the present invention includes calcium sulfate particles including 0.5 hydrate and the like and has a specific BET specific surface area, it is possible to shorten the induction period when manufacturing the ethylene oxide adduct. Furthermore, since the catalyst of the present invention is solid, the handling property is excellent during transporting and storing.

In addition, according to the method for manufacturing a catalyst of the present invention, a reaction product obtained by reacting the component (A) and the component (B) at a specific B/A ratio in the component (C) is produced, and this reaction product is separated from the component (C) and dried, thus, a catalyst capable of shortening the induction period in the manufacturing of the ethylene oxide adduct is manufactured. Furthermore, according to the method for manufacturing a catalyst of the present invention, a solid catalyst with an excellent handling property during transporting and storing is produced.

A shorter time is preferable for the induction period when producing ethylene oxide adducts and it is most preferable to have no induction period. In a case of manufacturing a fatty acid alkyl ester ethoxylate or alcohol ethoxylate as described above, for example, the induction period is preferably less than 1 hour, more preferably less than 30 minutes, even more preferably less than 10 minutes, and most preferably 0, that is, there is no induction period. Further, according to the catalyst of the present invention, it is possible to obtain an ethylene oxide adduct having a narrow ethylene oxide adduct distribution as compared with a case of using an alkali catalyst or the like. In addition, the production of by-products such as high molecular weight PEG is also suppressed.

EXAMPLES

A detailed description will be given below of the present invention with reference to Examples, but the present invention is not limited by the following description.
Raw Materials Used
Component (A)
  Calcium acetate monohydrate: Ikoma Fine Chemical Co., Ltd.
Component (B)
  Sulfuric acid: special grade reagent (concentration 96% by mass), manufactured by Kanto Chemical Co., Inc.
Component (C)
  2-propanol (IPA): special grade reagent, manufactured by Kanto Chemical Co., Inc.
  Methanol: special grade reagent, manufactured by Kanto Chemical Co., Inc.
(C') Component: Comparative Product of Component (C)
  Methyl laurate: Pastel M 12, manufactured by Lion Chemical Co., Ltd.
Starting Material for Ethoxylation Reaction
  Methyl laurate: same as above.
  Methyl myristate: Pastel M 14, manufactured by Lion Chemical Co., Ltd.

Lauryl alcohol (1-dodecanol): special grade reagent, manufactured by Wako Pure Chemical Industries, Ltd.

Catalyst Used in Comparative Example

Sodium hydroxide: special grade reagent, manufactured by Wako Pure Chemical Industries, Ltd.

Aluminum hydroxide magnesium: Kyowaad 300, manufactured by Kyowa Chemical Industry Co., Ltd.

Example 1

150 g of calcium acetate monohydrate and 525 g of IPA were added to a 1 L separable flask and stirred using a Disper stirring blade to obtain a dispersion (dispersing step). As stirring conditions, the rotating speed of the stirring blade was 3000 rpm, the stirring temperature was 20° C., and the stirring time was 20 minutes.

Thereafter, while continuing the stirring, 75 g of sulfuric acid (in terms of pure content) was added to the dispersion using a dropping funnel at a constant rate over a period of 1 hour, and calcium acetate monohydrate and sulfuric acid were mixed to produce a reaction product of both (reacting step). The reaction temperature was 15° C. to 25° C. In order to set the reaction temperature described above, the reaction was carried out while adjusting the temperature of the water bath. The molar ratio of sulfuric acid to calcium acetate monohydrate is 0.9.

After the addition of sulfuric acid, stirring was continued for 2 hours (aging step). The stirring temperature (aging temperature) was kept at 20° C.

Subsequently, the reaction product was suction filtered using a filter paper ("No. 5C" manufactured by Advantech Co., Ltd.) and separated from the IPA (separation operation). 100 g of the reaction product was placed in a beaker, 200 g of ethanol was added to the beaker and stirred (washing operation). Thereafter, a separating operation and a washing operation similar to those described above were repeated twice, and then a separating operation was performed to obtain a reaction product. Finally, the reaction product was placed in an electric furnace and dried at 50° C. for 2 hours to obtain a catalyst (drying step).

Through the above, the catalyst of Example 1 was produced.

Examples 2 to 8, Comparative Examples 1 to 5

Catalysts of Examples 2 to 4 and Comparative Example 4 were each produced in the same manner as in Example 1, except that the drying temperatures in the drying step were set as shown in Table 1.

Catalysts of Examples 5 to 7 and Comparative Example 3 were each produced in the same manner as in Example 1, except that the molar ratio of sulfuric acid to calcium acetate monohydrate was changed as shown in Table 1.

The catalyst of Example 8 was produced in the same manner as in Example 1, except that methanol was used instead of IPA in the dispersing step.

The catalyst of Comparative Example 2 was produced in the same manner as in Example 1, except that methyl laurate was used instead of IPA in the dispersing step.

The catalyst of Comparative Example 1 was manufactured by performing the dispersing step, the reacting step, and the aging step in the same manner as in Example 1. That is, the catalyst of Comparative Example 1 is a dispersion liquid including calcium sulfate which is a reaction product of calcium acetate monohydrate and sulfuric acid.

As the catalyst of Comparative Example 5, a commercially available calcium sulfate 0.5 hydrate (special grade reagent, manufactured by Kanto Chemical Co., Inc.) was used.

For each example catalyst, the measurement of the XRD and BET specific surface area was performed as follows. Since the catalyst of Comparative Example 1 is a dispersion liquid, these measurements are not performed.

Method for Measuring XRD

As the XRD measuring apparatus, "X'Pert PRO MRD" manufactured by PANalytical Co., Ltd., was used.

The catalyst of each example was ground in an agate mortar, filled in an aluminum sample holder, and measurement was carried out under the following conditions. The calcium sulfate types included in each catalyst were identified from the diffraction patterns of the obtained catalysts of each example. Specifically, it was identified that a 0.5 hydrate and the like was included in a catalyst for which a diffraction pattern similar to that in FIG. 1A was obtained and that a type II anhydrate was included in a catalyst for which a diffraction pattern similar to that in FIG. 1B was obtained. Here, none of the catalysts of the examples described above had a diffraction pattern similar to that of FIG. 1C.

Figure 2:
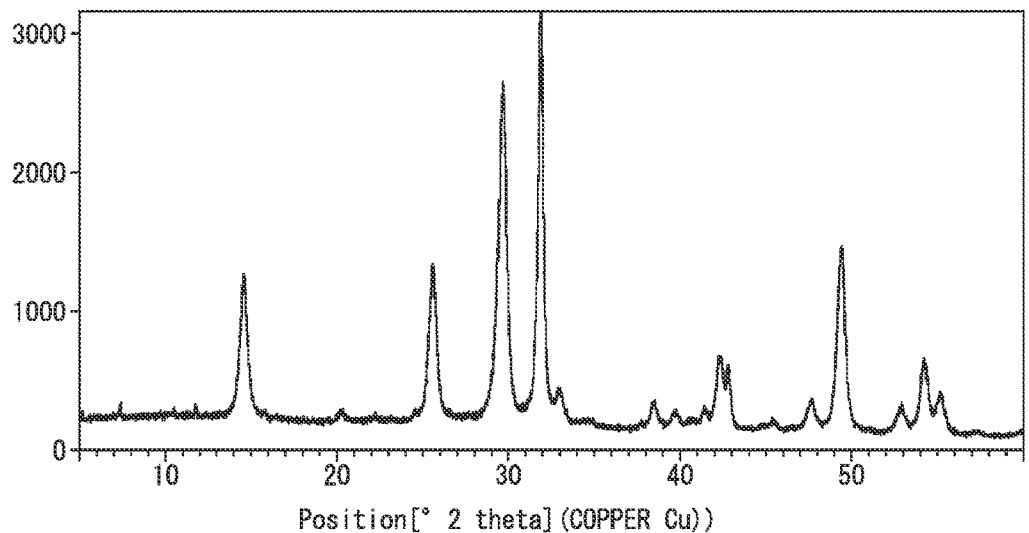
FIG. 2 is a diffraction pattern obtained when carrying out X-ray diffraction measurement on a catalyst of Example 1.
Figure 3:
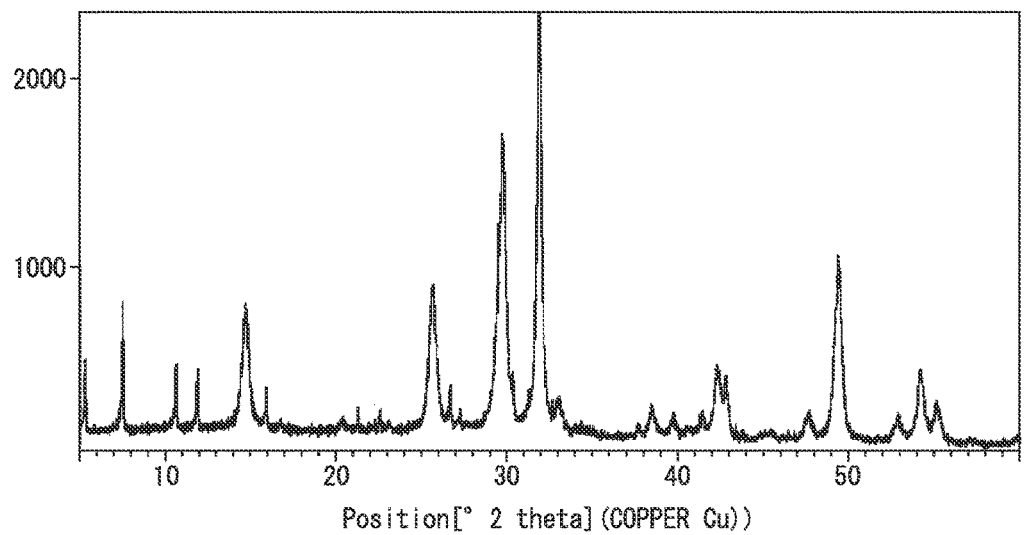
FIG. 3 is a diffraction pattern obtained when carrying out X-ray diffraction measurement on a catalyst of Example 6.
Figure 4:
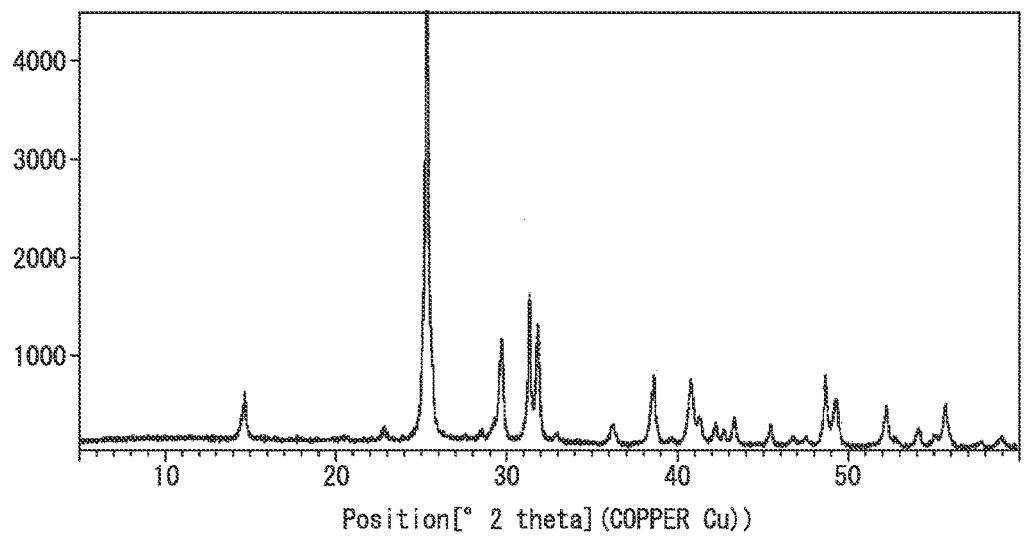
FIG. 4 is a diffraction pattern obtained when carrying out X-ray diffraction measurement on a catalyst of Comparative Example 3.
Figure 5:
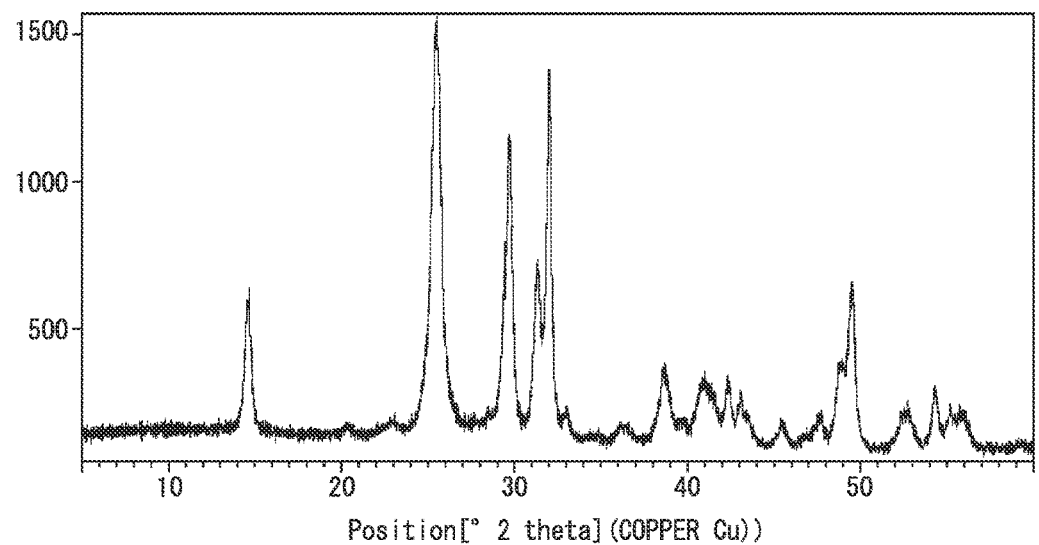
FIG. 5 is a diffraction pattern obtained when carrying out X-ray diffraction measurement on a catalyst of Comparative Example 4.
Figure 6:
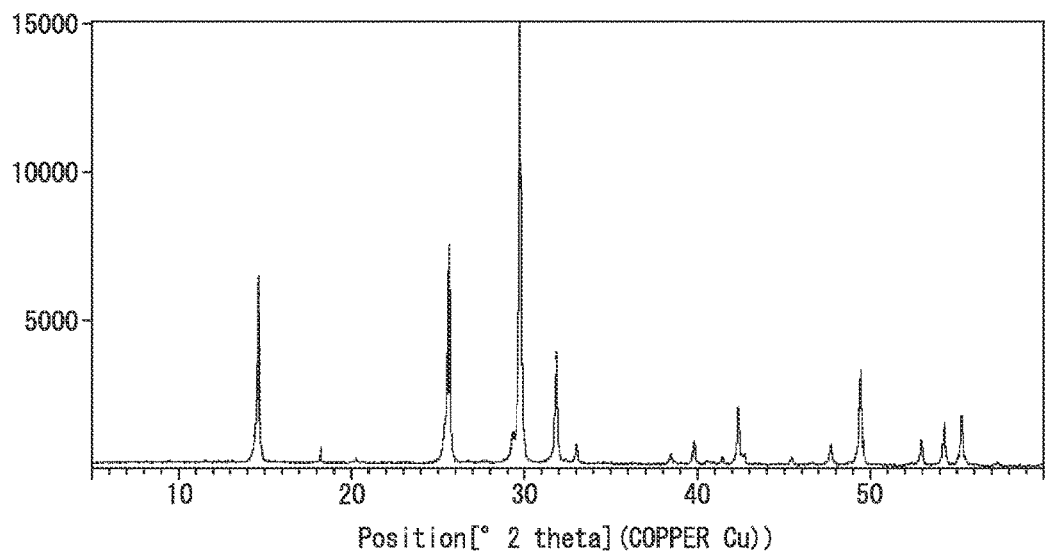
FIG. 6 is a diffraction pattern obtained when carrying out X-ray diffraction measurement on a catalyst of Comparative Example 5.

Table 1 shows the identification results of the catalysts of each example. For reference, the diffraction pattern of the catalyst of Example 1 is shown in FIG. 2, the diffraction pattern of the catalyst of Example 6 is shown in FIG. 3, the diffraction pattern of the catalyst of Comparative Example 3 is shown in FIG. 4, the diffraction pattern of the catalyst of Comparative Example 4 is shown in FIG. 5, and the diffraction pattern of the catalyst of Comparative Example 5 is shown in FIG. 6. It is understood that the catalysts of Comparative Examples 3 and 4 include type II anhydrates.

Measurement Conditions

Scan axis: Gonio

Measurement range: 5.0 to 8.0 [° 2θ]

X-ray output setting: tube current 40 mA, tube voltage 45 kV

Step size: 0.0170 [° 2θ]

Step time: 24.13 s

Irradiation width: 10.0 mm

Sample width: 10.0 mm

Emitting slit size: 1.0

Light receiving slit size: 0.1

Measurement temperature: 25° C.

Target: Cu

Spinner: yes

Method for Measuring BET Specific Surface Area

As an apparatus for measuring the BET specific surface area, "BELSORP-maxIIBELCAT" manufactured by MicrotracBEL Corp., which is a multi-point method BET specific surface area measuring apparatus was used.

Approximately 0.1 g of each example catalyst was weighed and filled in one of two equal capacity sample tubes of the above apparatus and the other was empty. Thereafter, the catalyst was cooled with liquid nitrogen to adsorb nitrogen to the catalyst, and the BET specific surface area was calculated from the difference from the empty tube. The measurement conditions were as follows.

The measurement results of the BET specific surface area of the catalyst of each example are shown in Table 1.

Measurement Conditions of BET Specific Surface Area

Pretreatment: 160° C., 60 minutes

Measurement mode: High precision (AFSM)

Adsorption temperature: 77 K

Measuring part device: Dewar bottle

Adsorbate name: nitrogen

Ethoxylation Reaction

An ethoxylation reaction of a fatty acid alkyl ester (mixture of methyl laurate and methyl myristate) was carried out using the catalyst of each example.

480 g of methyl laurate, 160 g of methyl myristate, 2.5 g of each example catalyst, and 14 g of IPA as a reaction accelerator were added to a 4 L autoclave provided with a Max Blend blade, and the mixture was stirred at a rotation speed of 420 rpm. Thereafter, nitrogen replacement was performed, and the temperature was raised to 180° C. Then, ethylene oxide (EO) was introduced until the internal pressure reached 0.5 MPa. At this time, when there is an induction period, the internal pressure does not decrease from 0.5 MPa. In this case, the introduction of EO was stopped and stirring was continued under the above conditions until the pressure was lowered. After that, the introduction of EO was restarted when the internal pressure started to drop. The time from stopping the introduction of EO to restarting was measured, and this time was taken as the induction period.

Furthermore, the time to complete the introduction of all of an amount of 15 moles of EO (1910 g) from the start of introduction of EO was measured, and this time was taken as the EO addition time.

The catalyst (dispersion liquid) of Comparative Example 1 was added to the autoclave such that the solid content was 2.5 g.

Table 1 shows the induction periods and EO addition times of the ethoxylation reactions carried out using the catalyst of each example.

In addition, the EO addition activity of the catalyst was determined according to the following evaluation criteria. ○ was a pass.

Table 1 shows the evaluation results of the EO addition activity.

Evaluation Criteria for EO Addition Activity
○: The induction period is less than 30 minutes and the EO addition time is less than 6 hours.
Δ: The induction period is 30 minutes or more to less than 60 minutes, and the EO addition time is less than 6 hours.
x: The induction period is 60 minutes or more, and/or the EO addition time is longer than 6 hours.

As shown in Table 1, there was no induction period in the ethoxylation reaction using the catalysts of Examples 1 to 8 to which the present invention was applied. Furthermore, the EO addition time was 3.5 to 4 hours.

On the other hand, in a case where the catalyst (dispersion liquid) of Comparative Example 1 was used, the induction period was 0.5 hours and the EO addition reaction time was 6 hours.

In a case of using the catalyst of Comparative Example 2 in which the BET specific surface area does not satisfy the range of the present invention, the induction period was 0.5 hours and the EO addition time was longer than 6 hours.

In a case of using the catalysts of Comparative Examples 3 and 4, which were type II anhydrates, the induction period was longer than 2 hours and the EO addition time was longer than 10 hours. In a case of using the catalyst of Comparative Example 5 which is a commercially available 0.5 hydrate, the induction period was longer than 2 hours and the EO addition time was longer than 10 hours.

From the above results, it was confirmed that the catalyst to which the present invention was applied had a shorter induction period. Furthermore, since the catalyst of the present invention is a solid, it is excellent in handling property during transporting and storing.

Adjustment of Al—Mg catalyst

Aluminum hydroxide magnesium hydroxide (Kyowaad 300, manufactured by Kyowa Chemical Industry Co., Ltd.) with a chemical composition formed of 2.5 MgO Al$_2$O$_3$ nH$_2$O was fired at 880° C. for 3 hours as the firing zone passing time using a tunnel type kiln to obtain a magnesium-aluminum composite metal oxide catalyst powder.

Example 9

400 g of lauryl alcohol and 1.2 g (0.3% by weight with respect to the alcohol) of the catalyst of Example 1 were added to an autoclave, the interior of the autoclave was replaced with nitrogen, and the temperature was raised while stirring. Then, 280 g of ethylene oxide (EO) was introduced while maintaining the temperature at 180° C. and the pressure at 0.3 MPa, and a reaction was carried out.

TABLE 1

| | | | | Example | | | | | | | Comparative Example | | | |
|---|---|---|---|---|---|---|---|---|---|---|---|---|---|---|
| | 1 | 2 | 3 | 4 | 5 | 6 | 7 | 8 | 1 | 2 | 3 | 4 | 5 |
| Identification results using XRD measurement | 0.5 hydrate | 0.5 hydrate | 0.5 hydrate | 0.5 hydrate | 0.5 hydrate | 0.5 hydrate | 0.5 hydrate | 0.5 hydrate | — | 0.5 hydrate | Type II an-hydrate | Type II an-hydrate | 0.5 hydrate |
| BET Specific Surface Area [m$^2$/g] | 109 | 54 | 44 | 40 | 82 | 60 | 40 | 64 | — | 26 | 47 | 43 | 3 |
| B/A molar ratio | 0.9 | 0.9 | 0.9 | 0.9 | 0.95 | 0.8 | 0.5 | 0.9 | 0.9 | 0.9 | 1 | 0.9 | — |
| Solvent (C) | IPA | IPA | IPA | IPA | IPA | IPA | IPA | Methanol | IPA | Methyl laurate | IPA | IPA | — |
| Drying temperature [° C.] | 50 | 100 | 200 | 300 | 50 | 50 | 50 | 50 | — | 50 | 50 | 400 | — |
| Evaluation induction period [h] | 0 | 0 | 0 | 0 | 0 | 0 | 0 | 0 | 0.5 | 0.5 | 2< | 2< | 2< |
| EO addition time [h] | 3.5 | 3.5 | 3.5 | 3.5 | 3.5 | 3.5 | 4 | 3.5 | 6 | 6< | 10< | 10< | 10< |
| EO addition activity | ○ | ○ | ○ | ○ | ○ | ○ | ○ | ○ | Δ | x | x | x | x |

Example 10

A reaction was carried out in the same manner as in Example 9 except that 663 g of ethylene oxide (EO) was introduced.

Comparative Example 6

400 g of lauryl alcohol and 1.2 g (0.3% by weight with respect to alcohol) of an Al—Mg catalyst were added to an autoclave, the interior of the autoclave was replaced with nitrogen, and the temperature was raised while stirring. Then, 280 g of ethylene oxide (EO) was introduced while maintaining the temperature at 180° C. and the pressure at 0.3 MPa, and a reaction was carried out.

Comparative Example 7

A reaction was carried out in the same manner as in Comparative Example 6 except that 663 g of ethylene oxide (EO) was introduced.

Comparative Example 8

400 g of lauryl alcohol and 2.4 g of 30% sodium hydroxide aqueous solution (0.6% by weight of sodium hydroxide with respect to the alcohol) were added to an autoclave, the interior of the autoclave was replaced with nitrogen, and the temperature was raised while stirring. Then, the water in the system was removed by stirring at 100° C. and 40 mmHg for 20 minutes, 280 g of ethylene oxide (EO) was introduced while maintaining the temperature at 180° C. and the pressure at 0.3 MPa, and a reaction was carried out.

Comparative Example 9

A reaction was carried out in the same manner as in Comparative Example 8 except that 663 g of ethylene oxide (EO) was introduced.

Method for Measuring Filtration Time 550 g of the reaction product synthesized in Examples 9 to 10 and Comparative Examples 6 to 7 were placed in a 1 L capacity separable flask and then 0.01 part by mass of aluminum sulfate as an aggregating agent with respect to 100 parts by mass of the reaction product, and 10 parts by mass of water with respect to 100 parts by mass of the reaction product were added and mixed at 420 rpm using paddle stirring blades at a temperature of 80° C. for 1 hour to produce aggregates and obtain a mixed solution including the aggregates.

Next, an aqueous solution of 1 mol/L potassium hydroxide (special grade reagent, manufactured by Kanto Chemical Co., Inc.) was added to the mixed solution to adjust the pH to 7.0, and the mixture was cooled to 50° C.

Next, 200 g of the mixed solution was placed in a pressurized filter in which a filter 123 B (manufactured by 3M Japan Ltd., filtration precision 1 μm) having a diameter of 40 mm was mounted, pressurized with nitrogen to 0.1 MPa, filtered, and the aggregates were separated from the reaction product and a purified product of lauryl alcohol ethoxylate was obtained.

The time required from the start of the filtration until the separation of the aggregates was taken as the filtration time.

Method for Measuring EO Adduct Distribution

The distribution of the addition molar number of EO (EO adduct distribution) in the crude reaction product was determined by a high-performance liquid chromatography (HPLC) method, and the results thereof are shown in the table. The conditions of the HPLC method are the following measurement conditions, and the EO adduct distribution is calculated by the following calculation method. The larger the value of the EO adduct distribution, the narrower the distribution of the EO addition molar number.

Measurement Conditions of HPLC Method

High Performance Liquid Chromatograph: manufactured by Hitachi, Ltd.

Column: Inertsil C8 5 Micro manufactured by GL Science (4.6×250 mm)

Mobile phase: acetonitrile/water=60/40 (vol/vol), flow rate 1 mL/min.

Detector: differential refractive index detector L-7490 (manufactured by Hitachi, Ltd.), 40° C.

Injection volume: 200 μL.

Temperature: 15° C.

Calculation Method

The EO adduct distribution was calculated by the following equation.

{(Area of maximum peak (P1) derived from lauryl alcohol)+(total area of two peaks before and after maximum peak P1)}÷total peak area Method for Measuring Amount of Polymer Polyethylene Glycol (High Molecular Weight PEG)

The content of the high molecular weight PEG in the crude reaction product was measured by gel permeation chromatography (GPC) method, and the weight average molecular weight was 10,000 or more as the high molecular weight PEG. The measurement conditions of the GPC method are as follows. The results are shown in the table.

Measurement Conditions of GPC Method

Column: ShodexAsahipak GF-310 HQ, manufactured by Showa Denko K.K.

Detector: differential refractive index detector RID-10A, manufactured by Shimadzu Corp.

TABLE 2

|  |  | Example | | Comparative Example | | | |
|---|---|---|---|---|---|---|---|
|  |  | 9 | 10 | 6 | 7 | 8 | 9 |
| Identification results using XRD measurement |  | 0.5 hydrate | 0.5 hydrate | — | — | — | — |
| BET Specific Surface Area [m²/g] |  | 109 | 109 | 152 | 152 | — | — |
| B/A molar ratio |  | 0.9 | 0.9 | — | — | — | — |
| Solvent (C) |  | IPA | IPA | — | — | — | — |
| Drying temperature [° C.] |  | 50 | 50 | — | — | — | — |
| Evaluation | Induction period [h] | 0 | 0 | 0 | 0 | 0 | 0 |
|  | EO addition time [h] | 0.5 | 1 | 1 | 1.5 | 1 | 1.5 |

TABLE 2-continued

|  | Example | | Comparative Example | | | |
|---|---|---|---|---|---|---|
|  | 9 | 10 | 6 | 7 | 8 | 9 |
| EO addition activity | ○ | ○ | ○ | ○ | ○ | ○ |
| EO adduct distribution [area %] | 78.1 | 77.9 | 81.6 | 80.5 | 60.7 | 40.9 |
| High molecular weight PEG amount [mass %] | <0.01 | <0.01 | 0.3 | 0.4 | <0.01 | <0.01 |
| Filtration time [seconds] | 10 | 10 | 60 | 100 | — | — |

As shown in Table 2, in the ethoxylation reaction using the catalysts of Examples 9 to 10 to which the present invention was applied, the amount of high molecular weight PEG was reduced compared with Comparative Examples 6 to 7 using an Al—Mg catalyst, and it was possible to greatly shorten the filtration time. In addition, the EO adduct distribution of the ethoxylation reaction product using the catalysts of Examples 9 to 10 to which the present invention was applied was as narrow as that of Comparative Examples 6 to 7 using an Al—Mg catalyst, and was narrower than that of Comparative Examples 8 to 9 using a sodium hydroxide catalyst.

From the above results, it was confirmed that the catalyst to which the present invention is applied makes it possible to reduce the amount of high molecular weight PEG and to shorten the filtration time compared with a case where Al—Mg catalyst and sodium hydroxide are used as a catalyst, and to obtain an alkylene oxide adduct of an alcohol having a narrow EO adduct distribution.

INDUSTRIAL APPLICABILITY

According to the ethoxylation catalyst of the present invention, the induction period is further shortened and the handling property is excellent.

What is claimed is:

1. An ethoxylation catalyst having a BET specific surface area of 40 to 150 $m^2/g$, the catalyst comprising:
    calcium sulfate particles including at least one kind of compound selected from the group consisting of calcium sulfate 0.5 hydrate and type III anhydrous calcium sulfate.

2. A method for manufacturing an ethoxylation catalyst, the method comprising:
    mixing at least one compound (A) selected from the group consisting of a calcium salt of carboxylic acid, calcium oxide, and calcium hydroxide with a sulfuric acid (B) in a solvent (C) to produce a reaction product of (A) and (B);
    separating the reaction product from the solvent (C); and
    drying the separated reaction product at a drying temperature of less than 400° C.;
    wherein the solvent (C) consists essentially of one or more alcohols each having 1 to 6 carbon atoms, and
    a molar ratio of (B) to (A) added to the solvent (C) in the reacting step is from 0.5 to 0.99.

3. The method for manufacturing an ethoxylation catalyst according to claim 2, wherein the drying temperature in the drying step is 50° C. to 350° C.

* * * * *